(12) United States Patent
Arakawa (10) Patent No.: US 6,765,226 B2
(45) Date of Patent: Jul. 20, 2004

(54) RADIATION IMAGE READOUT APPARATUS

(75) Inventor: Satoshi Arakawa, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 310 days.

(21) Appl. No.: 09/987,372

(22) Filed: Nov. 14, 2001

(65) Prior Publication Data

US 2002/0056818 A1 May 16, 2002

(30) Foreign Application Priority Data

Nov. 14, 2000 (JP) ........................................ 2000-346816

(51) Int. Cl.$^7$ .............................................. G03B 42/08
(52) U.S. Cl. ..................................... 250/586; 250/581
(58) Field of Search ............................... 250/581, 582, 250/583, 584, 585, 586, 484.4

(56) References Cited

U.S. PATENT DOCUMENTS

| 4,816,679 A | 3/1989 | Sunagawa et al. ........ 250/327.2 |
| 4,922,103 A | 5/1990 | Kawajiri et al. .......... 250/327.2 |
| 5,801,391 A | * 9/1998 | Arakawa et al. ............ 250/584 |

FOREIGN PATENT DOCUMENTS

| JP | 60-111568 | 6/1985 | ............ H04N/1/04 |
| JP | 60-236354 | 11/1985 | ............ H04N/1/04 |

* cited by examiner

Primary Examiner—Constantine Hannaher
Assistant Examiner—Timothy Moran
(74) Attorney, Agent, or Firm—Sughrue Mion, PLLC

(57) ABSTRACT

A radiation image readout apparatus for reading out, by use of a line sensor formed of a plurality of photoelectric converting elements arranged in a straight line, a radiation image stored on a stimulable phosphor sheet etc., wherein the occurrence of a Moiré effect in the final image is controlled by preventing feedback distortion, is provided. A focusing optical system formed of a first lens array for causing a stimulated emission to become a parallel luminous flux and a second lens array for focusing the parallel luminous flux onto a dichroic mirror and line sensor for transmitting the parallel flux is provided. The refraction ratio of the second lens array and the positional relation of the second Selfoc lens array and the dichroic mirror are adjusted so that the MTF is 50% or less of the Nyquist frequency determined by the width of the direction X of the photoelectric converting elements.

14 Claims, 10 Drawing Sheets

SECT. I-I

RADIATION IMAGE READOUT APPARATUS

BACKGROUND OF THE INVENTION

1. Field of the Invention

The present invention relates to a radiation image readout apparatus for reading out, by use of a line sensor formed of a plurality of photoelectric converting elements arranged in a straight line, a radiation image stored on a stimulable phosphor sheet or the like.

2. Description of the Related Art

There are known stimulable phosphors, which upon the irradiation thereof by radiation store a portion of the radiation energy, and emit upon the subsequent irradiation thereof with a visible or other excitation light a stimulated emission corresponding to the stored radiation energy. Radiation image readout apparatuses employing, for example, stimulable phosphor sheets, which utilize these stimulable phosphors in a layer containing stimulable phosphors which has been formed on a substrate, to temporarily record the radiation image data of the radiation that has passed through a human body or other subject of photographing, upon the irradiation thereof by a radiation, are in wide use as CR (Computed Radiography) apparatuses.

An image signal obtained by the system described above is subjected to image processing such as gradation processing, frequency processing, etc. appropriate to diagnostic reading, after which the processed image signal is recorded on a film as a visible diagnostic image (final image), or displayed on a high-resolution CRT monitor for diagnostic reading by a doctor.

Further, in accordance with the radiation image readout apparatus utilizing the stimulable phosphor sheet described above and with a view to making the apparatus compact and of reduced cost, a line light source is used as an excitation light source for irradiating the sheet with an excitation light in a line form, together with a line sensor formed of a plurality of photoelectric converting elements arranged in a straight line along the lengthwise direction of the line-shaped portions of a stimulable phosphor sheet that has been irradiated with an excitation light emitted from the line light source (hereinafter referred to as the main scanning direction); a scanning means for moving the line light source and line sensor from one end of the stimulable phosphor sheet to the other end in the direction substantially perpendicular to the lengthwise direction of the line-shaped portions (hereinafter referred to as the sub-scanning direction) (refer to Japanese Unexamined Patent Publication Nos. 60(1985)-111568, 60(1985)-236354, and 1(1989)-101540).

However, when a stimulated emission based on a radiation image is received by use of a line sensor formed of a plurality of photoelectric converting elements arranged in a straight line, because the photoelectric converting elements are arranged at a uniform pitch, the stimulated emission is sampled at every pixel; accordingly, at this time, for cases in which the signal component of the stimulated emission received by the line sensor, based on a radiation image scanned by the line light source, includes a signal component having a frequency higher than ½ the sampling frequency (hereinafter referred to as the Nyquist frequency), a Moiré effect is caused in the final image, whereby the image quality thereof is deteriorated.

SUMMARY OF THE INVENTION

The radiation image readout apparatus according to the present invention has been developed in consideration of the circumstances described above, and it is a primary objective of the present invention to provide a radiation image readout apparatus for reading out, by use of a line sensor formed of a plurality of photoelectric converting elements arranged in a straight line, a radiation image stored on a stimulable phosphor sheet or the like, wherein the occurrence of a Moiré effect in the final image is controlled by preventing distortion due to feedback.

The first radiation image readout apparatus according to the present invention comprises: a illuminating means for illuminating with an excitation light in a line form a portion of the surface of a stimulable phosphor sheet on which a radiation image has been stored; a focusing optical system provided with a focusing lens for focusing the stimulated emission emitted from a portion of the stimulable phosphor sheet upon the illumination thereof by the excitation light emitted from the illuminating means in a line form and a detecting means provided with a line sensor, which is formed of a plurality of photoelectric converting elements arranged in a straight line and at a uniform pitch, for receiving and photoelectrically converting a stimulated emission focused by the focusing optical system; a scanning means for moving the illuminating means and the detecting means relatively from one end of the stimulable phosphor sheet to another in a direction differing from that of the lengthwise direction of the illuminated portions, wherein the MTF of the focusing optical system is 50% or less of the Nyquist frequency determined by the aforementioned uniform pitch.

Here, the referent of "the focusing lens of the focusing optical system" is not limited to being a single lens, but includes systems provided with a plurality of focusing lenses, as well as systems provided with elements for performing an optical function other than focusing.

Figure 4:
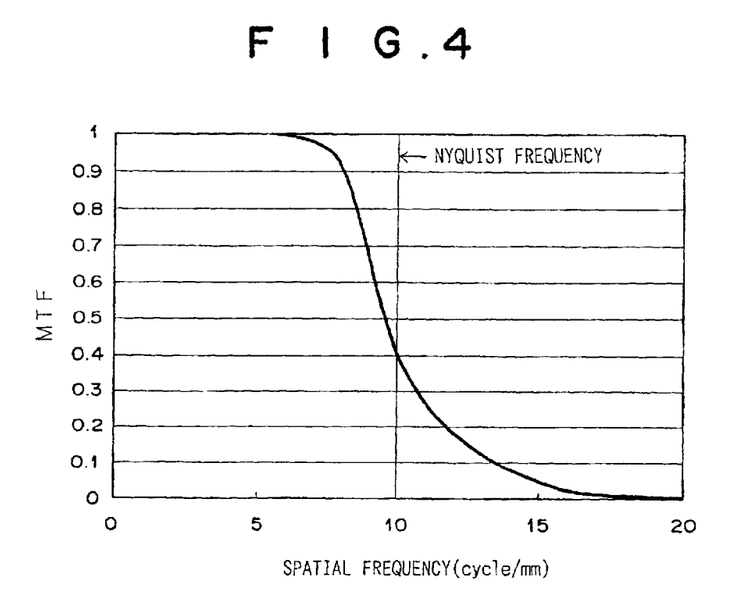
FIG. 4 shows the MTF of the focusing optical system (50% or less of the Nyquist frequency) employed in the first embodiment.

Further, the referent of "the MTF of the focusing optical system" as shown in FIG. 4, for example, falls in inverse proportion to the rising of the frequency of the signal component of a stimulated emission based on a radiation image. Further, the phrase "the Nyquist frequency determined by the aforementioned uniform pitch" refers to the frequency equivalent to ½ the sampling frequency, which is determined by the pitch at which the photoelectric converting elements of the line sensor are disposed. Generally, if there is a signal component having a frequency higher than the Nyquist frequency, distortion due to feedback is produced. The expression "the MTF of the focusing optical system is 50% or less of the Nyquist frequency determined by the aforementioned uniform pitch" means that the signal component occurring in the Nyquist frequency is caused to become 50% or less by the MTF of the focusing optical system.

Figure 5:
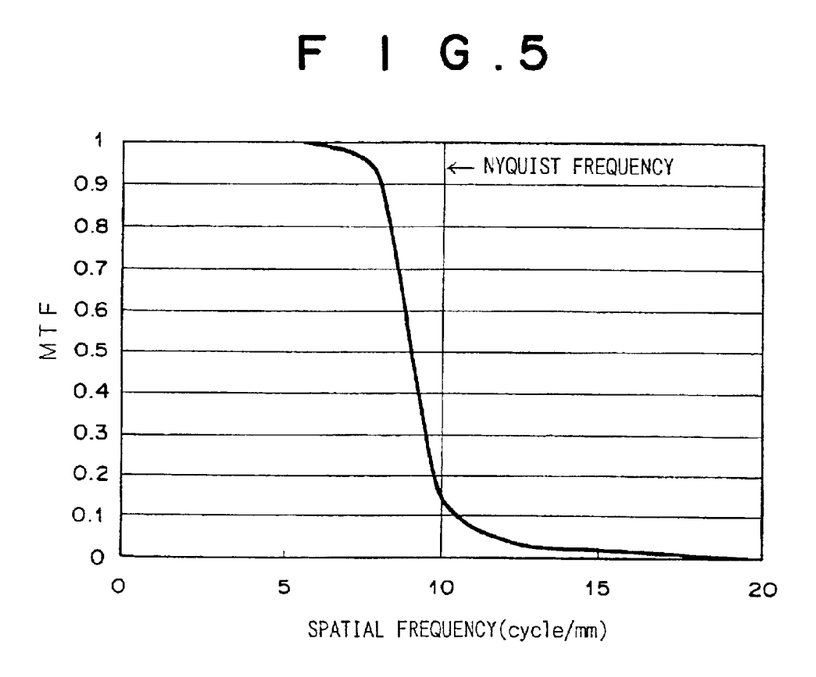
FIG. 5 shows the MTF of the focusing optical system (20% or less of the Nyquist frequency) employed in the first embodiment.

Still further, the MTF of the focusing optical system can also be caused to be 20% or less of the Nyquist frequency determined by the aforementioned uniform pitch, as shown in FIG. 5.

The second radiation image readout apparatus according to the present invention comprises: a illuminating means for illuminating with an excitation light in a line form a portion of the surface of a stimulable phosphor sheet on which a radiation image has been stored; a focusing optical system provided with a focusing lens for focusing the stimulated emission emitted from a portion of the stimulable phosphor sheet upon the illumination thereof by the excitation light emitted from the illuminating means in a line form; a detecting means provided with a line sensor, which is formed of a plurality of photoelectric converting elements arranged in a straight line and at a uniform pitch, for receiving and photoelectrically converting a stimulated emission focused by the focusing optical system; a scanning means for moving the illuminating means and the detecting means relatively from one end of the stimulable phosphor sheet to another in a direction differing from that of the lengthwise direction of the illuminated portions; and a readout means for reading out the output of the line sensor in the order corresponding to the movement thereof, and obtaining the data forming the final image; wherein the aforementioned uniform pitch is less than the width of the pixels of the final image; further comprising a pixel-density converting filter for converting the image signal of the pixel density output from the line sensor based on the aforementioned uniform pitch to the pixel density of the final image; wherein the frequency characteristic of the pixel-density converting filter is caused to be 50% or less of the Nyquist frequency determined by the pixel density of the final image.

Here, the expression "the aforementioned uniform pitch is less than the width of the pixels of the final image" refers to the raising of the sampling frequency by causing the aforementioned uniform pitch to be narrower than the width occurring in the main scanning direction of the pixels of the final image so as to reduce the distortion due to feedback. Further, the referent of "the frequency characteristic of the pixel-density converting filter" is, for example, the characteristic whereby the frequency range converted by the pixel-density converting filter falls in inverse proportion to the rising of the frequency of the signal component of a stimulated emission based on the radiation image shown in FIG. 8, for example. Further, the expression "the Nyquist frequency determined by the pixel density of the final image" is the frequency that is ½ of the sampling frequency determined by the width occurring in the main scanning direction of the pixels of the final image. The expression "the frequency characteristic of the pixel-density converting filter is caused to be 50% or less of the Nyquist frequency determined by the pixel density of the final image" refers to the causing, according to the frequency characteristic of the pixel-density converting filter, of the signal component of the stimulated emission occurring in the Nyquist frequency to be 50% or less when the converting of the pixel density occurring in the main scanning direction is performed thereby.

Note that because the frequency characteristic of the pixel-density converting filter is determined by the filtering coefficient and the number of filter taps thereof, a desired frequency characteristic can be realized by selecting an appropriate filtering coefficient and number of filter taps.

Figure 9:
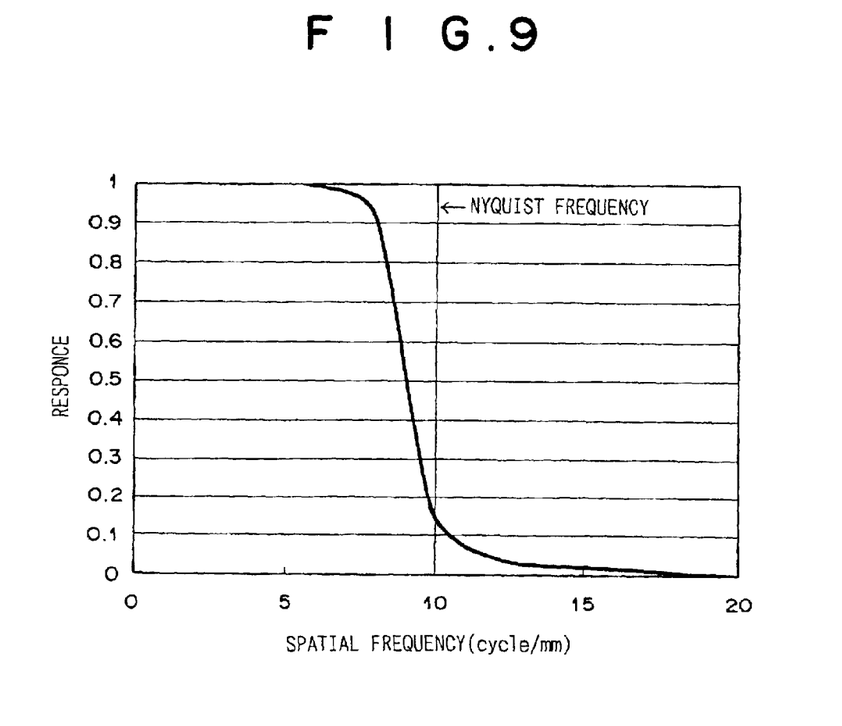
FIG. 9 shows the frequency characteristic of the pixel-density converting filter (20% or less of the Nyquist frequency) employed in the first embodiment.

Further, the frequency characteristic of the pixel-density converting filter can also be caused to be 20% or less of the Nyquist frequency determined by the pixel density of the final image, as shown in FIG. 9.

Still further, according to the first and second radiation image readout apparatuses of the present invention: the width of the interval in which the stimulable phosphor sheet is relatively moved in the direction relative to the portions that have been illuminated by the excitation light in a line form, is narrower than the width of the pixels of the final image; a second pixel-density converting filter is provided for converting to the pixel density of the final image the image signal of the pixel density based on the width of the interval in the direction in which the illuminated portions outputted by the line sensor are relatively moved; and the frequency characteristic of the second pixel-density converting filter can be caused to be 50% or less of the Nyquist frequency determined by the width of the pixels of the final image.

Figure 10:
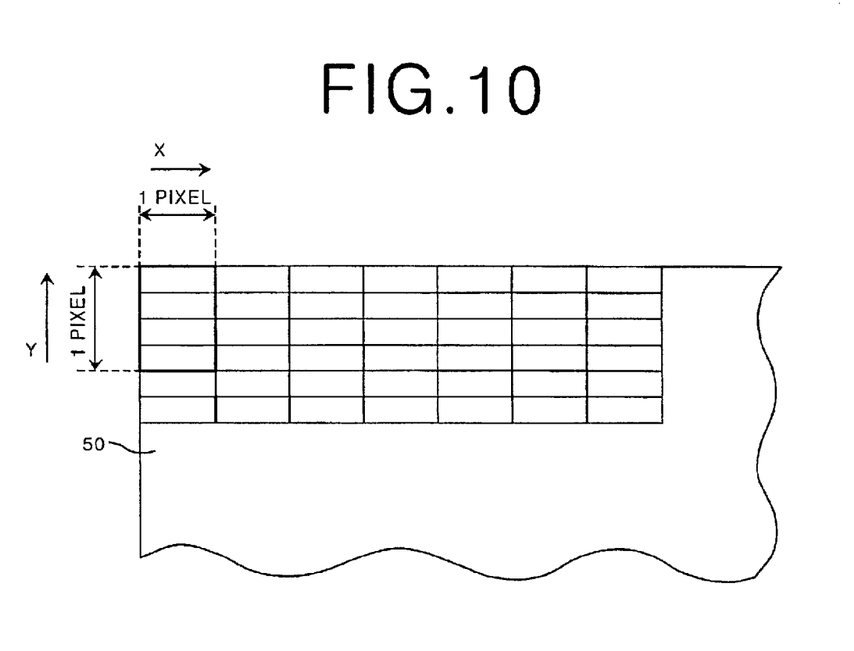
FIG. 10 is a drawing illustrating the pixel density conversion that occurs in the sub-scanning direction.

Here, the expression "the width of the interval in which the stimulable phosphor sheet is moved in the direction relative to the portions that have been illuminated by the excitation light in a line form, is narrower than the width of the pixels of the final image" means that, as shown in FIG. 10, the width of the sub-scanning direction (the direction Y) of the portions of the stimulable phosphor sheet that have been illuminated by the excitation light in a line form is smaller than the width of one pixel (in FIG. 10, ¼ the width of a pixel).

Accordingly, the expression "for converting to the pixel density of the final image the image signal of the pixel density based on the width of the interval in the direction in which the illuminated portions outputted by the line sensor are relatively moved" means that the image signal of one pixel of the final image is converted so that the sub-scanning direction (the direction Y) of the portions of the sheet illuminated by the excitation light is configured of a plurality of image signal areas into which the width thereof has been divided.

Further, the expression "the Nyquist frequency determined by the pixel density of the final image" refers to the frequency that is equivalent to ½ the scanning frequency determined by the width of the pixels occurring in the sub-scanning direction of the final image. Further, the expression "the frequency characteristic of the of the second pixel-density converting filter can be caused to be 50% or less of the Nyquist frequency determined by the width of the pixels of the final image" refers to the causing of the signal component occurring in the Nyquist frequency to be 50% or less due to said frequency characteristic when the pixel density occurring in the sub-scanning direction is converted by the pixel-density converting filter of the second radiation image readout apparatus according to the present invention.

Further still, the frequency characteristic of the second pixel-density converting filter can be caused to be 20% or less of the Nyquist frequency determined by the pixel density of the final image, as shown in FIG. 9, for example.

According to the first radiation image readout apparatus of the present invention, because the MTF of the focusing optical system for focusing the stimulated emission, which is based on a radiation image, emitted from a stimulable phosphor sheet upon the illumination thereof by an excitation light is caused to be less than 50% of the Nyquist frequency determined by the uniform pitch at which the photoelectric converting elements of the line sensor are disposed, the distortion due to feedback can be reduced, and the occurrence of a Moiré effect in the final image can thereby be controlled.

Further, for cases in which the MTF of the focusing optical system has been caused to be 20% or less of the Nyquist frequency determined by the aforementioned uniform pitch, the distortion due to feedback can be further reduced, and the occurrence of a Moiré effect in the final image can thereby be controlled.

According to the second radiation image readout apparatus of the present invention: the width of the pitch of the photoelectric converting elements of the line sensor for receiving the stimulated emission emitted from the stimulable phosphor sheet upon the illumination thereof with the excitation light is made to be narrower than the width of the pixels of the final image, whereby the Nyquist frequency is raised; a pixel-density converting filter is provided for converting the pixel density of the image signal obtained by the reception and photoelectrical conversion by the line sensor of the stimulated emission to the desired pixel density of the final image; and because the frequency characteristic of the of the pixel-density converting filter has been caused to be 50% or less of the Nyquist frequency, which is determined by the pixel density of the pixels of the final image, the distortion due to feedback can be reduced, and the occurrence of a Moiré effect in the final image can thereby be controlled.

Further, for cases in which the frequency characteristic of the of the pixel-density converting filter has been caused to be 20% or less of the Nyquist frequency determined by the aforementioned uniform pitch, the distortion due to feedback can be further reduced, and the occurrence of a Moiré effect in the final image can thereby be controlled.

According to the first and second radiation image readout apparatuses of the present invention: the width of the interval in the direction in which a portion of the stimulable phosphor sheet that has been illuminated with the excitation light in a line form is relatively moved is narrower than the width of the pixels of the final image; a second pixel-density converting filter is provided for converting the pixel density based on the width of the direction in which the image signal output by the line sensor is relatively moved to the pixel density of the final image; for cases in which the frequency characteristic of the of the second pixel-density converting filter has been caused to be 50% or less of the Nyquist frequency determined by the width of the pixels of the final image, distortion due to feedback occurring in the pixel-density conversion occurring in the sub-scanning direction can also be reduced, and the occurrence of a Moiré effect in the final image can be further controlled.

Further, for cases in which the frequency characteristic of the of the second pixel-density converting filter has been caused to be 20% or less of the Nyquist frequency determined by the width of the pixels of the final image, the occurrence of a Moiré effect in the final image can be more effectively controlled in the same manner as described above.

DESCRIPTION OF THE PREFERRED EMBODIMENTS

Figure 1:
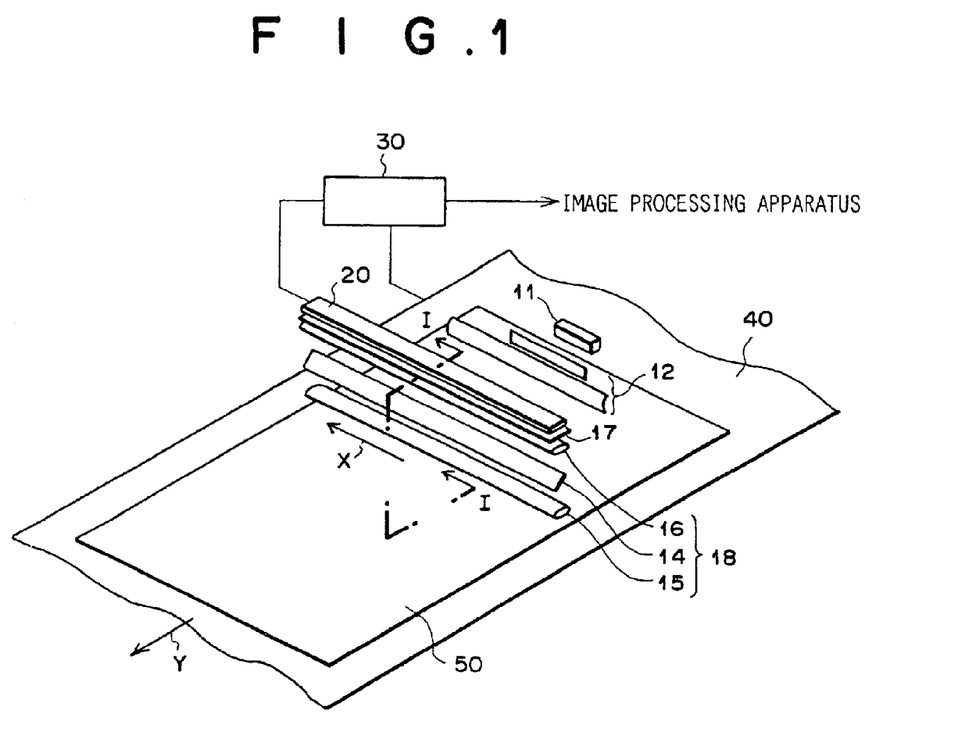
FIG. 1 is a schematic drawing of an embodiment of the first radiation image readout apparatus according to the present invention.
Figure 2:
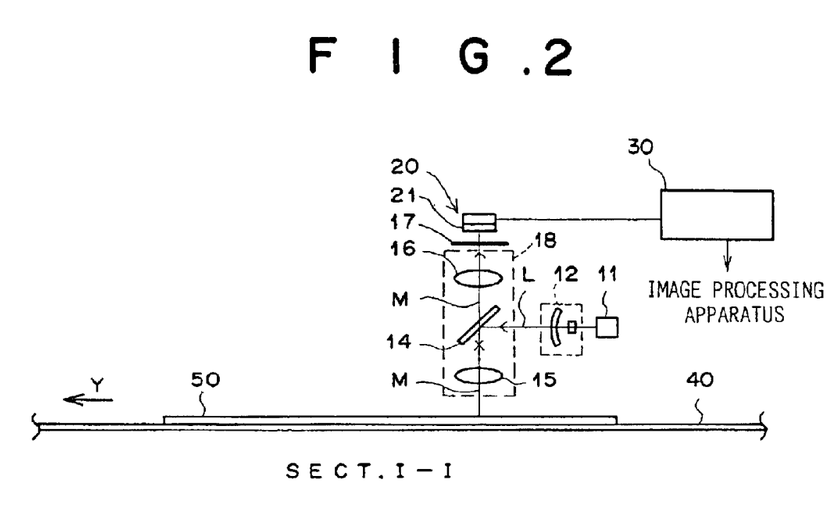
FIG. 2 is a cross-sectional view along the line I—I of the radiation image readout apparatus shown in FIG. 1.
Figure 3:
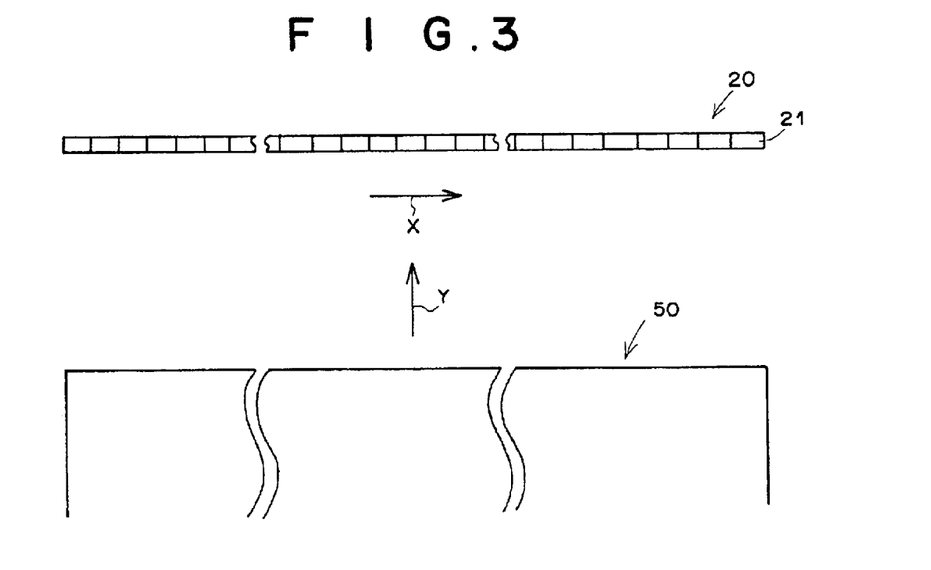
FIG. 3 is a detailed schematic drawing of the line sensor employed in the radiation image readout apparatus shown in FIGS. 1 and 2.

Hereinafter the preferred embodiments of the present invention will be explained with reference to the attached drawings. A first embodiment of the radiation image readout apparatus according to the present invention is shown in FIGS. 1 and 2. FIG. 1 shows a perspective view of an embodiment of the first radiation image readout apparatus, and FIG. 2 shows a cross-sectional view along the line I—I of the radiation image readout apparatus shown in FIG. 1. Further, FIG. 3 is a detailed schematic drawing of the line sensor 20 employed in the radiation image readout apparatus shown in FIGS. 1 and 2.

The first radiation image readout apparatus according to the present invention comprises: a scanning belt 40 onto which a stimulable phosphor sheet 50 (hereinafter referred to as a phosphor sheet) on which a radiation image has been cumulatively stored is loaded and which conveys said phosphor sheet 50 in the direction indicated by the arrow Y; an excitation light source 11 for projecting an excitation light L in a 2-dimensional line form (hereinafter referred to simply as excitation light) onto a surface of the phosphor sheet 50 in a direction substantially parallel thereto; an optical system 12 formed of an assembly consisting of collimator lens and a toric lens, which unidirectionally expands a beam of light; a dichroic mirror 14, which is disposed at a 45 degree angle with respect to the surface of the phosphor sheet 50, for reflecting the excitation light L in a substantially perpendicular direction toward the phosphor sheet 50 so as to transmit the stimulated emission M, which is described below; a lens array 15 (a lens formed of a plurality of refractive index distribution lenses, and hereinafter referred to as a first Selfoc lens array), which is a refractive index distribution type lens array for focusing the excitation light L reflected by the dichroic mirror 14 in a line form extending in the direction X on the phosphor sheet 50, and converting the stimulated emission M emitted from the phosphor sheet 50 upon the irradiation thereof by the excitation light and which corresponds to the radiation energy stored on said phosphor sheet 50 to a parallel light flux; a second Selfoc lens array 16 for focusing onto a line sensor 20, which is described below, the stimulated emission M that has been converted to a parallel light flux by the first Selfoc lens array 15 and reflected by the dichroic mirror 14; an excitation light cutoff filter 17 for cutting off the small amount of the excitation light L reflected from the surface of the phosphor sheet 50 that becomes mixed with the stimulated emission M transmitted by the second Selfoc lens array 16, and transmitting the stimulated emission M; a line sensor 20 for receiving and photoelectrically converting the stimulated emission M transmitted by the excitation light cutoff filter 17; and an image readout means 30 for reading out the signal outputted from the line sensor 20.

As to the excitation light source, a light source that emits an excitation light in a line form, or a light source that employs an optical system to focus the excitation light emitted therefrom into a line form can be used.

Further, the optical system 12 formed of the aforementioned collimator lens and toric lens expands the excitation light emitted from the excitation light source 11 onto a desired irradiation area on the phosphor sheet 50.

The line sensor 20, in more detail, as shown in FIG. 3, is formed of a plurality of photoelectrical converting elements 21 (e.g., 1,000 or more elements) aligned along the direction X.

Further, the second Selfoc lens 16 array serves as an imaging surface onto which the image formed by the stimulated emission M occurring above the phosphor sheet 50 is focused at a 1 to 1 correspondence.

Still further, as shown in FIG. 4, the refractive indexes of the first and second Selfoc lens arrays and the positional relation between the first and second Selfoc lenses and the dichroic mirror 14 of the focusing optical system 16 formed of the first Selfoc lens array 15, which causes the stimulated emission M to become a parallel light flux, and the second Selfoc lens array 16, which focuses the stimulated emission M that has been converted to a parallel light flux by the first Selfoc lens array onto the dichroic mirror for transmitting the stimulated emission M and the line sensor 20, are adjusted so that the MTF of the focusing optical system 12 is 50% or less of the Nyquist frequency determined by the width in the Direction X of the photoelectrical converting elements 21.

Next, the operation of the radiation image readout apparatus according to the current embodiment will be explained. First, by moving the scanning belt 40 in the direction of the arrow Y, the phosphor sheet 50 that has been loaded onto the scanning belt 40 and on which has been a radiation image recorded is conveyed in the direction of the arrow Y. At this time, the conveyance speed of the phosphor sheet 50 is equal to that of the scanning belt 40, and the speed of the belt 40 is input to the image readout means 30.

On the other hand, the excitation light source 11 projects the line-form excitation light L in a direction substantially parallel with respect to the surface of the phosphor sheet 50. This excitation light L is converted to a parallel beam by the optical system 12 formed of the collimator lens and the toric lens disposed on the optical path thereof, and reflected by the dichroic mirror 14 in a perpendicular direction so as to enter the phosphor sheet 50 at a right angle; this reflected light is caused to become a line-form beam extending in the direction X and to enter said phosphor sheet 50 at a right angle by the first Selfoc lens array 15.

Upon the irradiation of the focusing zone of the phosphor sheet 50 by the excitation light L, the excitation light L excites the stimulable phosphors located within said focusing zone; then, the excitation light L is dispersed within the phosphor sheet 50 and also excites the stimulable phosphors located in the vicinity of said focusing zone. As a result, a high-intensity stimulated emission M corresponding to the radiation image that has been cumulatively recorded on the phosphor sheet 50 is emitted from said focusing zone and the vicinity thereof. This stimulated emission M is converted to a parallel light flux and by the first Selfoc lens array 15, transmitted by the dichroic mirror 14, and focused onto the photoelectric converting elements 21 of the line sensor 20 by the second Selfoc lens array 16. At this time, even if a small amount of the excitation light L reflected from the surface of the phosphor sheet 50 is included in the stimulated emission M transmitted by the second Selfoc lens array 16, because the excitation light cutoff filter cuts off said reflected component of the excitation light L included in the stimulated emission M transmitted by the second Selfoc lens array 16, said reflected excitation light L does not enter the surface of the line sensor 20. Further, because the refractive ratio of the first Selfoc lens array 15 and the second Selfoc lens array 16 and the positional relation between the first Selfoc lens array 15 and the second Selfoc lens array 16 and the dichroic mirror 14 have been adjusted so that the MTF of the focusing optical system 18 is 50% or less of the Nyquist frequency determined by the width in the direction X of the photoelectrical converting elements 21, the production of distortion due to feedback when the stimulated emission M is received and sampled by the photoelectrical converting elements 21 of the line sensor 20.

The stimulated emission M is photoelectrically converted by the line sensor 20, and the image signal obtained thereby is read out by the image readout means 30 and output to an image processing apparatus or the like.

Further, although according to the current embodiment the MTF of the focusing optical system 18 has been caused to be 50% or less of the Nyquist frequency determined by the width in the direction X of the photoelectrical converting elements 21, it is desirable that the MTF be 20% or less of the Nyquist frequency determined by the width in the direction X of the photoelectrical converting elements 21, as shown in FIG. 5.

According to the first radiation image readout apparatus of the present invention, because the MTF of the focusing optical system 18 that focuses the stimulated emission M, which is based upon a radiation image, emitted from the phosphor sheet 50 upon the irradiation thereof by the excitation light L onto the line sensor 20 has been caused to be 50% or less of the Nyquist frequency determined by the width in the direction X of the photoelectrical converting elements 21, distortion due to feedback can be reduced, and the occurrence of a Moiré effect in the final image can be controlled.

Further, for cases in which the MTF of the focusing optical system 18 is 20% or less of the Nyquist frequency determined by the width in the direction X of the photoelectrical converting elements 21, the distortion due to feedback can be further reduced, and the occurrence of Moiré in the final image can be controlled.

Figure 6:
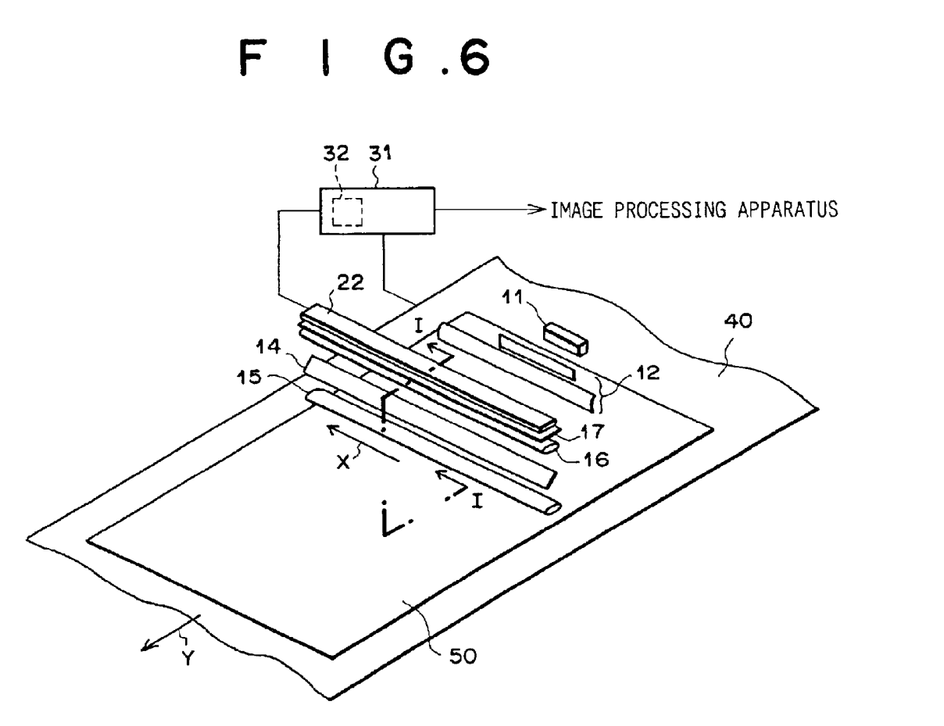
FIG. 6 is a schematic drawing of an embodiment of the second radiation image readout apparatus according to the present invention.
Figure 7:
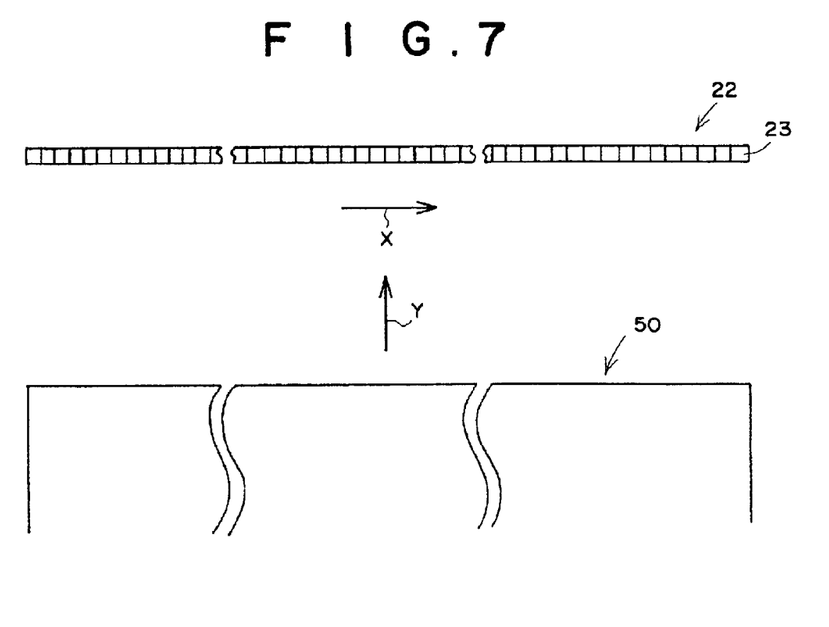
FIG. 7 is a detailed schematic drawing of the line sensor employed in the radiation image readout apparatus shown in FIG. 5.

Next, an embodiment of the second radiation image readout apparatus according to the present invention will be explained. FIG. 6 is a schematic drawing of the second radiation image readout apparatus according to the present invention. FIG. 7 is a detailed drawing of the configuration of the line sensor 22 shown in FIG. 6. Because the configuration thereof is substantially the same as that of the line sensor 20 occurring in the above-described embodiment, only elements not in common therewith that are shown in FIGS. 6 and 7 have been assigned reference numbers. Note that in so far as it is not particularly required, further explanation of the elements in common with the above-described embodiment of the first radiation image readout apparatus according to the present invention has been omitted.

According to the radiation image readout apparatus of the current embodiment, the width in the direction X of the photoelectrical converting elements 23 of the line sensor 22 for receiving and photoelectrically converting the stimulated emission emitted from the phosphor sheet 50 is narrower than the width of the pixels of a desired image.

Further, the image readout means for reading out the image signal obtained by the photoelectrical conversion of the stimulated emission by the photoelectrical converting elements 23 of the line sensor 22 is provided with a pixel-density converting filter 32 for converting the pixel density of the read out image signal to the pixel density of a desired image.

Note that because the frequency characteristic of the pixel-density converting filter 32 is determined by the filtering coefficient or the number of filter taps, a desired frequency characteristic can be obtained by selecting an appropriate filtering coefficient or number of filter taps.

Next, the operation of the second radiation image readout apparatus according to the present invention will be explained. According to the radiation image readout apparatus of the current embodiment, the stimulated emission emitted from the phosphor sheet 50 is received and photoelectrically converted by the line sensor 22 formed of the photoelectrical converting elements 23 having a width narrower than the pixel density of a desired image, and the image signal obtained thereby is readout by the image readout means 31. At this time, because the width of the direction X of the photoelectrical converting elements 23 has been configured so as to be narrower than the pixel density of a desired image, distortion caused by feedback during sampling by the line sensor 22 can be reduced.

Accordingly, after the pixel density of the image signal read out by the image readout means 31 has been converted to the pixel density of a desired image, said image signal of which the pixel density has been converted to the pixel density of a desired image is digitized, etc., and outputted to an image processing apparatus or the like.

Here, because the frequency characteristic of the pixel-density converting filter 32 is configured so as to be 50% or less of the Nyquist frequency determined by the pixel density of a desired image, the distortion due to the feedback accompanying the pixel-density conversion processing can be reduced.

Further, although according to the current embodiment the frequency characteristic of the pixel-density converting filter 32 has been caused to be 50% or less of the Nyquist frequency determined by the pixel density of a desired image, it is desirable that the frequency characteristic of the pixel-density converting filter 32 be 20% or less of the Nyquist frequency determined by the pixel density of a desired image, as shown in FIG. 9.

According to the first radiation image readout apparatus of the present invention: the width of the photoelectrical converting elements 23 of the line sensor 22 for receiving and photoelectrically converting the stimulated emission emitted from the phosphor sheet 50 upon the illumination thereof by the excitation light L is caused to be narrower than the width of the pixel density of a desired image and the Nyquist frequency is raised thereby; a pixel-density converting filter 32 is provided for converting the pixel density of the image signal obtained by the reception and photoelectrical conversion of the stimulated emission M by the line sensor 22 to the pixel density of the final image; and because the frequency characteristic of the pixel-density converting filter 32 is configured so as to be 50% or less of the Nyquist frequency determined by the pixel density of the final image, the distortion due to the feedback can be reduced, and the occurrence of a Moiré effect in the final image controlled.

Further, for cases in which the frequency characteristic of the pixel-density converting filter 32 is configured so as to be 20% or less of the Nyquist frequency determined by the pixel density of the final image, the distortion due to feedback can be further reduced, and the occurrence of a Moiré effect in the final image can be controlled.

Figure 8:
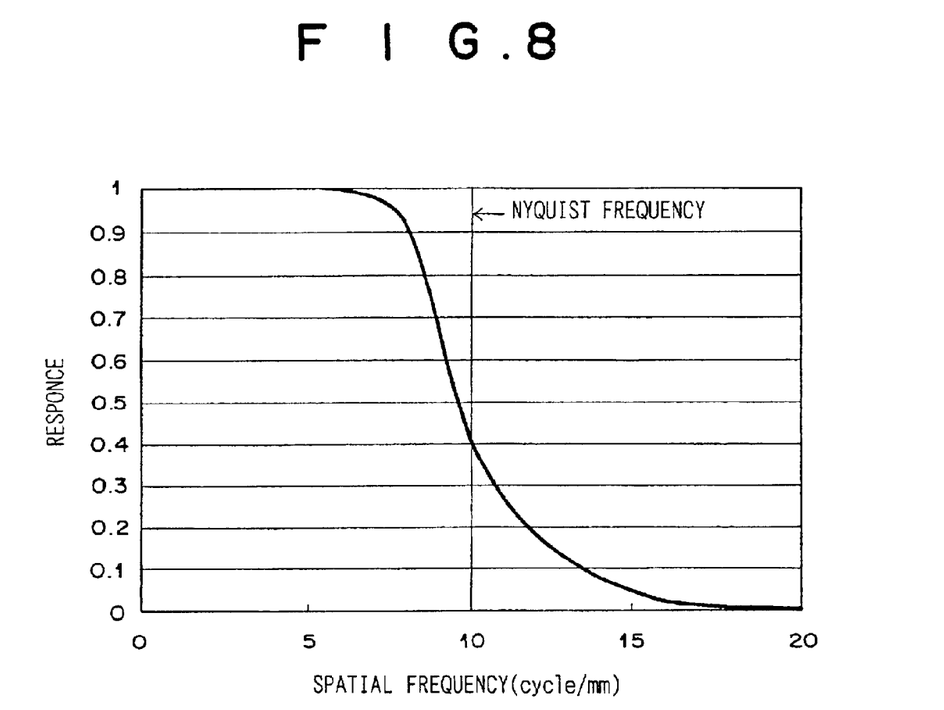
FIG. 8 shows the frequency characteristic of the pixel-density converting filter (50% or less of the Nyquist frequency) employed in the first embodiment.

Still further, according to the embodiments of the first and second radiation image readout apparatuses of the present invention, as shown in FIG. 8, the width in the direction Y of a portion of the stimulable phosphor sheet that has been illuminated by the excitation light in a line form is narrower than the pixel density of a desired image, and a second pixel-density converting filter for converting the pixel density based on the width of a portion of the phosphor sheet that has been illuminated by the excitation light in a line form to the pixel density of a desired image can be further provided. At this time, the frequency characteristic of the second pixel-density converting filter can be configured so as to be 50% or less of the Nyquist frequency determined by the pixel density of a desired image. In addition, it is desirable that the frequency characteristic of the second pixel-density converting filter is configured so as to be 20% or less of the Nyquist frequency determined by the pixel density of a desired image; in this way, even during the pixel-density conversion processing occurring in the direction Y, distortion due to feedback can be reduced.

Note that the radiation image readout apparatus according to the present invention is not limited to the above-described embodiments; various known configurations can be adopted for the light source, the focusing optical system disposed between the light source and the phosphor sheet, the optical system disposed between the phosphor sheet and the line sensor, and the line sensor. Further, a configuration further comprising an image signal processing apparatus for subjecting the signal read out by the image data readout means to a variety of signal processing processes, or a configuration further comprising an erasing means for adequately erasing the radiation energy remaining on a phosphor sheet that has been completely irradiated by the excitation light can be adopted.

What is claimed is:

1. A radiation image readout apparatus, comprising:
   an illuminating means for illuminating with an excitation light in a line form a portion of the surface of a stimulable phosphor sheet on which, a radiation image has been stored,
   a focusing optical system provided with a focusing lens for focusing the simulated emission emitted from a portion of the stimulable phosphor sheet upon the illumination thereof by the excitation light emitted from the illuminating means in a line form and a detecting means provided with a line sensor, which is formed of a plurality of photoelectric converting elements arranged in a straight line and at a uniform pitch, for receiving and photoelectrically converting a stimulated emission focused by the focusing optical system,
   a scanning means for moving the illuminating means the detecting means relatively from one end of the stimulable phosphor sheet to another in a direction different from that of the lengthwise direction of the illuminated portions, wherein
   the MTF of the focusing optical system is 50% or less at the Nyquist frequency determined by the aforementioned uniform pitch.

2. A radiation image readout apparatus as defined in claim 1, wherein
   the MTF of the focusing optical system is 20% or less at the Nyquist frequency determined by the aforementioned uniform pitch.

3. A radiation image readout apparatus, comprising
   an illuminating means for illuminating with an excitation light in a line form a portion of the surface of a stimulable phosphor sheet on which a radiation image has been stored,
   a focusing optical system provided with a focusing lens for focusing the stimulated emission emitted from a portion of the stimulable phosphor sheet upon the illumination thereof by the excitation light emitted from the illuminating means in a line form and a detecting means provided with a line sensor, which is formed of a plurality of photoelectric converting elements arranged in a straight line and at a uniform pitch, for receiving and photoelectrically converting a stimulated emission focused by the focusing optical system, a scanning means for moving the illuminating means and the detecting means relatively from one end of the stimulable phosphor sheet to another in a direction differing from that of the lengthwise direction of the illuminated portions, and a readout means for reading out the output of the line sensor in the order corresponding to the movement thereof, and obtaining the data forming the final image, wherein said uniform pitch is less than the width of the pixels of the final image, further comprising a pixel-density converting filter for converting the image signal of the pixel density outputted form the line sensor based on said uniform pitch to the pixel density of the final image, wherein the frequency characteristic of the pixel-density converting filter is 50% or less at the Nyquist frequency determined by the pixel density of the final image.

4. A radiation image readout apparatus as defined in claim 3, wherein the frequency characteristic of the pixel-density converting filter is 20% or less at the Nyquist frequency determined by the pixel density of the final image.

5. A radiation image readout apparatus as defined in either of claims 1 or 3, wherein the width of the interval of the direction in which the portions of the stimulable phosphor sheet that have been illuminated with the excitation light in a line form are relatively moved is narrower than the width of the pixels of the final image, further comprising a second pixel-density converting filter is provided for converting the pixel density based on the width of the interval in the direction in which the image signal output by the line sensor is relatively moved to the pixel density of the final image, wherein the frequency characteristic of the second pixel-density converting filter is 50% or less at the Nyquist frequency determined by the pixel density of the final image.

6. A radiation image readout apparatus as defined in claim 5, wherein the frequency characteristic of the second pixel-density converting filter can be caused to be 20% or less at the Nyquist frequency determined by the pixel density of the final image.

7. A radiation image readout apparatus, comprising:

illumination means comprising an excitation light for exciting a radiation image which has been stored in a stimulable medium;

focusing means for focusing a stimulated emission from said stimulable medium;

detection means for detecting radiation image emissions comprising photoelectric conversion elements arranged at a known regularity; and scanning means for moving: i) said stimulable medium relative to said illumination means and said detection means, or ii) said illumination means and said detection means relative to said stimulable medium; wherein an MTF of the focusing means is 50% or less at a Nyquist frequency derived from said known regularity of said photoelectric conversion elements.

8. The radiation image readout apparatus of claim 7, further wherein the MTF of the focusing means is 20% or less at said Nyquist frequency.

9. The radiation image readout apparatus of claim 7, further comprising pixel-density conversion means for converting an image signal of the pixel density output from the detection means to a pixel density of a final image.

10. The radiation image readout apparatus of claim 9, further wherein the frequency characteristic of the pixel-density conversion means is 50% or less at a Nyquist frequency determined by a pixel density of a final image.

11. The radiation image readout apparatus of claim 9, further wherein the frequency characteristic of the pixel-density conversion means is 20% or less at a Nyquist frequency determined by a pixel density of a final image.

12. The radiation image readout apparatus of claim 7, further wherein said known regularity is less than the width of the pixels of a final image.

13. The radiation image readout apparatus of claim 7, further wherein:

a width of the interval of the direction in which portions of said stimulable medium that have been illuminated with said excitation light are relatively moved is narrower than the width of the pixels of a final image; and further comprising pixel-density converting means for converting the pixel density of the width of the interval of the direction in which portions of said stimulable medium that have been illuminated with said excitation light are relatively moved to the pixel density of a final image; wherein the frequency characteristic of the pixel-density converting means is 50% or less at a Nyquist frequency determined by a pixel density of a final image.

14. The radiation image readout apparatus of claim 13, wherein the frequency characteristic of the pixel-density converting means is 20% or less at the Nyquist frequency determined by the pixel density of the final image.

* * * * *